US00PP34254P2

(12) United States Plant Patent
Sasso

(10) Patent No.: US PP34,254 P2
(45) Date of Patent: May 17, 2022

(54) ***ECHEVERIA* PLANT NAMED 'SERENA'**

(50) Latin Name: ***Echeveria* hybrid**
Varietal Denomination: Serena

(71) Applicant: Ovata B. V., Bleiswijk (NL)

(72) Inventor: Bruno Sasso, Bordighera (IT)

(73) Assignee: Ovata B. V., Bleiswijk (NL)

( * ) Notice: Subject to any disclaimer, the term of this patent is extended or adjusted under 35 U.S.C. 154(b) by 131 days.

(21) Appl. No.: 16/893,531

(22) Filed: Jun. 5, 2020

(30) Foreign Application Priority Data

Nov. 27, 2019 (QZ) ..... PBR 2019/3109

(51) Int. Cl.
*A01H 6/32* (2018.01)
*A01H 5/00* (2018.01)

(52) U.S. Cl.
USPC ..... Plt./373

(58) Field of Classification Search
USPC ..... Plt./373
See application file for complete search history.

(56) References Cited

PUBLICATIONS

Pluto Plant Variety Database Jan. 23, 2021. p. 1.*

* cited by examiner

*Primary Examiner* — Annette H Para
(74) *Attorney, Agent, or Firm* — Samuel R. McCoy, Jr.

(57) ABSTRACT

A new and distinct variety of *Echeveria* plant named 'Serena' which is characterized by relaxed succulent foliage in a stemless rosette, glaucescent greyed-purple foliage with a pink hue, and a foliar aspect which varies from convex to concave with an upturned leaf tip thus creating a wavy appearance. The new variety has shown to be uniform and stable in the resulting generations from asexual propagation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'Serena'.

CROSS REFERENCE TO RELATED APPLICATIONS

This application claims priority to the Community Plant Variety Rights application number 2019/3109, filed on Nov. 27, 2019, which is herein incorporated by reference.

BACKGROUND OF THE INVENTION

Parentage: 'Serena' is a naturally-occurring, whole-plant mutation of an unnamed *Echeveria gibbiflora* x *elegans* hybrid plant (not patented) which was discovered by the inventor in March of 2009 at a commercial greenhouse in Bordighera, Italy. The mutation was noted for its purple foliage with a wavy appearance.

Asexual Reproduction: Asexual reproduction of the new cultivar 'Serena', by way of rooting leaf cuttings, was first initiated in March of 2009 at a commercial greenhouse in Bleiswijk, the Netherlands. Through eight subsequent generations, the unique features of this cultivar have proven to be stable and true to type.

SUMMARY OF THE INVENTION

The cultivar 'Serena' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Serena'. These characteristics in combination distinguish 'Serena' as a new and distinct *Echeveria* cultivar:

1. 'Serena' exhibits relatively relaxed succulent foliage arranged in a basal rosette; and
2. 'Serena' exhibits inverted carinate foliage which varies from convex to concave, creating a wavy appearance, with the leaf tip curled upward.
3. 'Serena' exhibits glaucescent greyed-purple foliage with a pink hue and pink margins.

BOTANICAL DESCRIPTION OF THE PLANT

Figure 1:
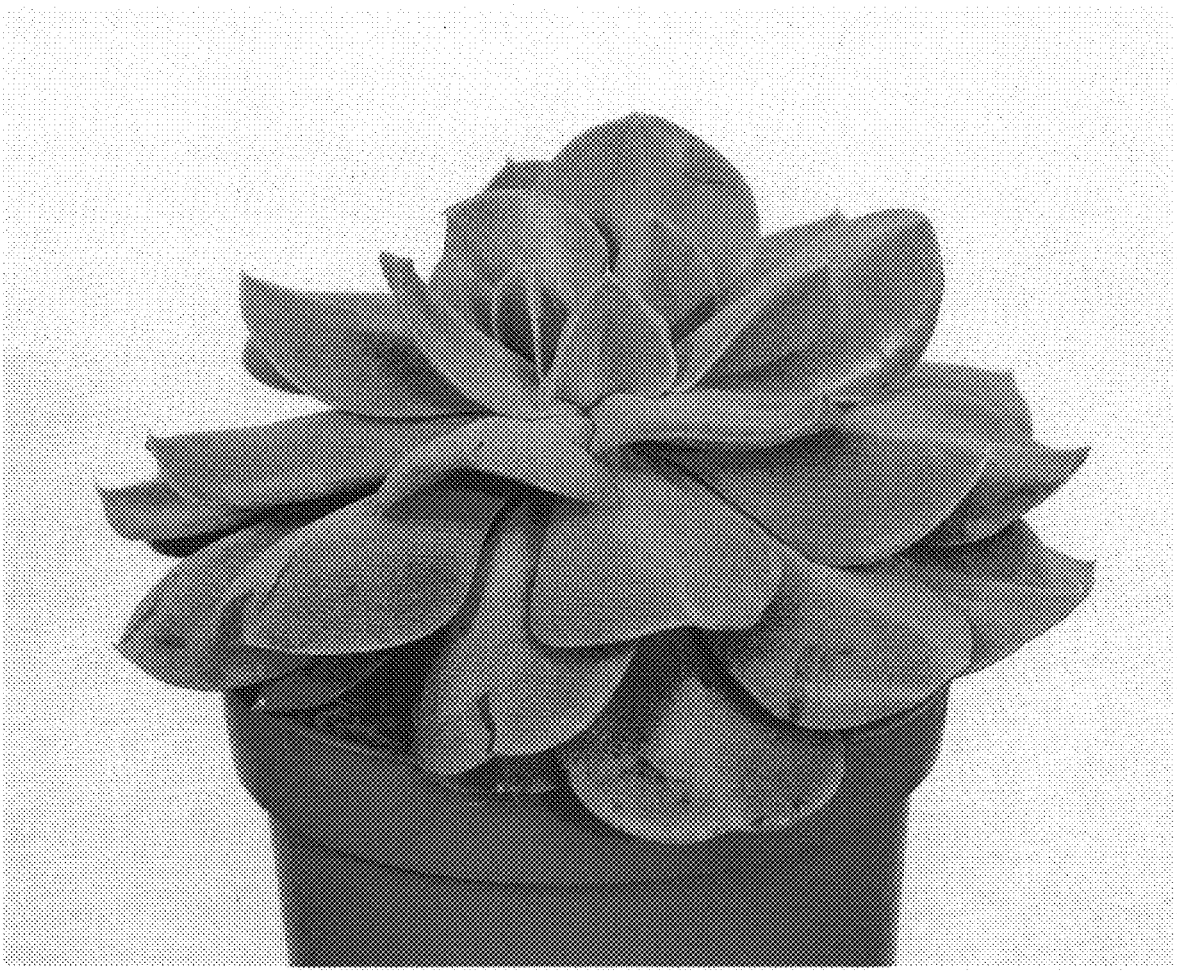
FIG. 1 illustrates, as nearly true as it is reasonably possible to make the same in color photographs of this type, an exemplary plant of 'Serena' grown in a commercial greenhouse in Bleiswijk, the Netherlands. This plant is approximately 1 year old, shown planted in a 12 cm container.
Figure 2:
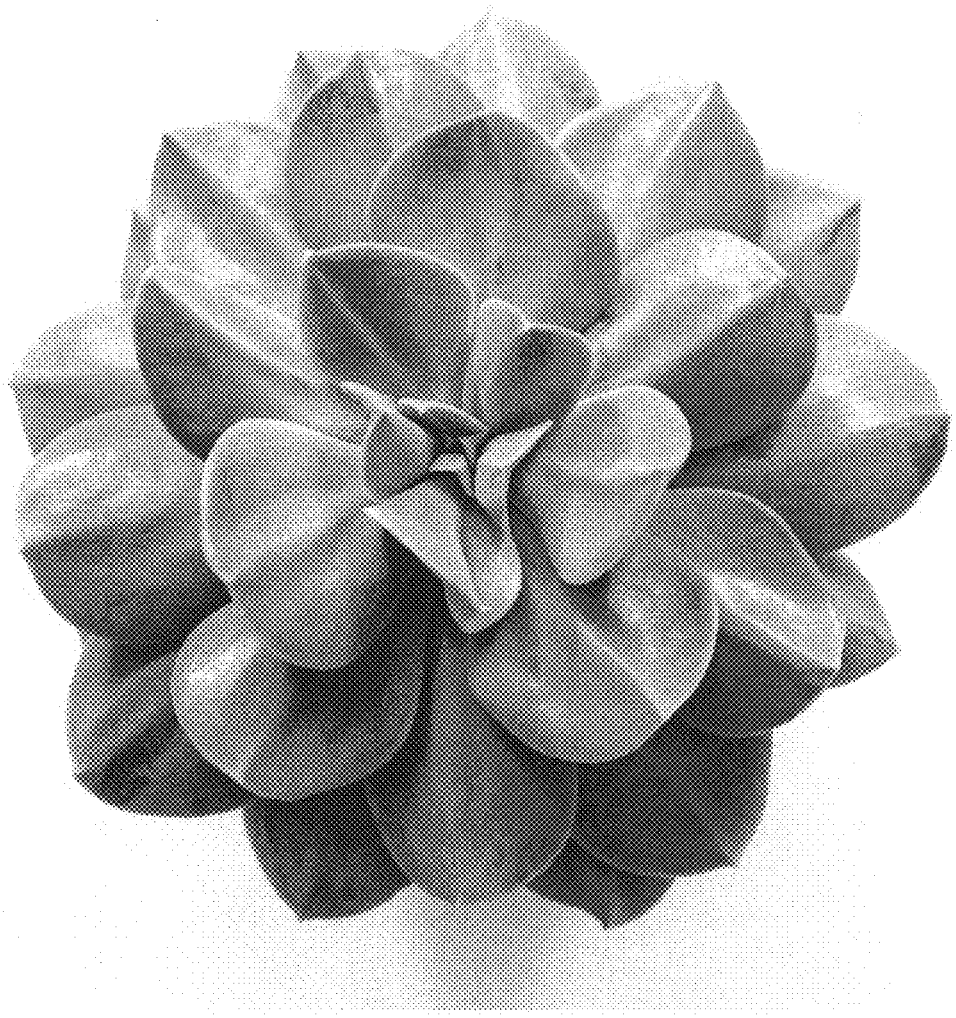
FIG. 2 illustrates, as nearly true as it is reasonably possible to make the same in color photographs of this type, the typical foliage arrangement of 'Serena'.
Figure 3:
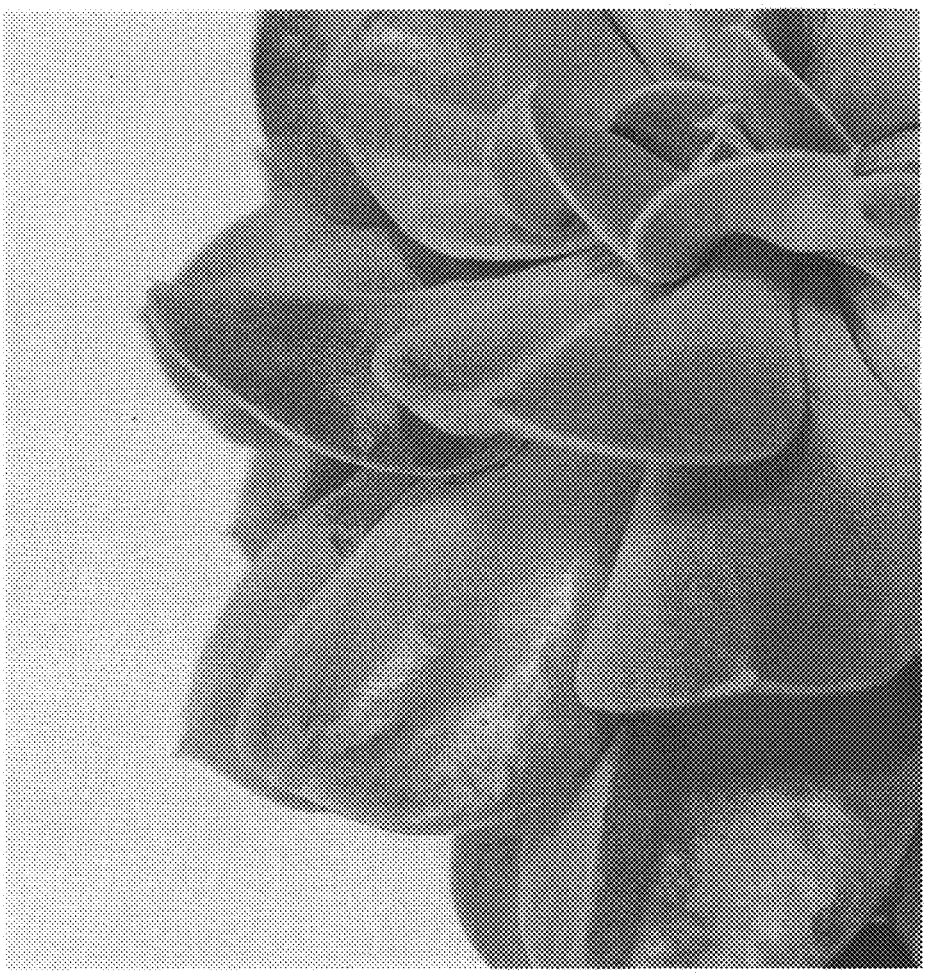
FIG. 3 illustrates, as nearly true as it is reasonably possible to make the same in color photographs of this type, the adaxial surface of the mature foliage 'Serena'.
Figure 4:
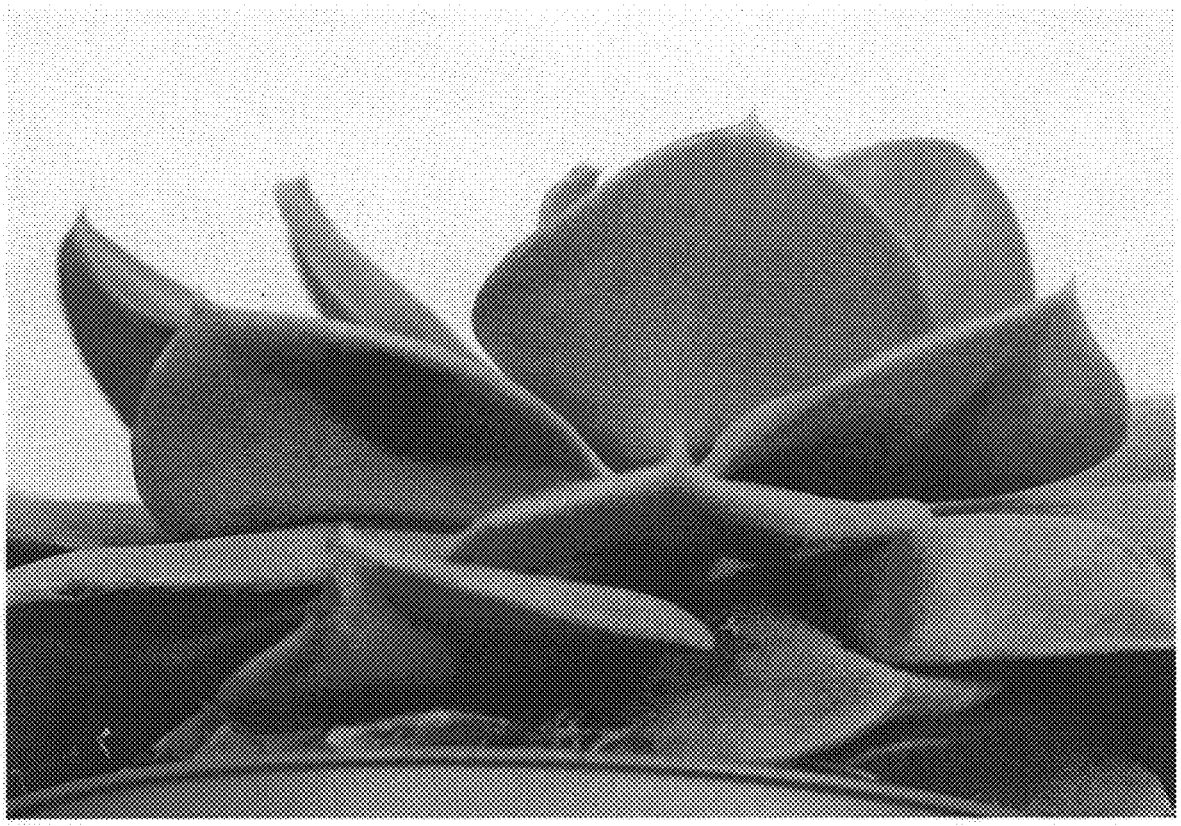
FIG. 4 illustrates, as nearly true as it is reasonably possible to make the same in color photographs of this type, the abaxial surface of the mature foliage 'Serena'.

The following observations and measurements made in November of 2019 describe averages from a sample set of six specimens of 1 year old 'Serena' plants grown in 12 cm nursery containers at commercial greenhouse in Bleiswijk, the Netherlands. Plants were produced using conventional greenhouse production protocols for *Echeveria* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'Serena' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'Serena' and a comparison with the parent and closest known comparator is provided below.

Plant description:

*Growth habit*.—Succulent perennial with foliage growing in a non-branched basal rosette.

*Plant form*.—Flattened globular.

*Height from soil level to top of foliar plane*.—7.8 cm.

*Plant spread*.—Average of 16.7 cm.

*Growth rate*.—Moderately fast.

*Plant vigor*.—Moderately vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 12 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Rosette.

*Division*.—Simple.

*Attachment*.—Sessile.

*Quantity*.—Approximately 46 leaves per rosette.

*Shape*.—Obovate to nearly spatulate.

*Dimensions*.—7.1 cm long, 4.0 cm wide, and 0.6 cm thick, on average.

*Aspect*.—Slightly inverted carinate to moderately inverted carinate; moderately concave to moderately convex with leaf tip curled upward.

*Attitude*.—Leaves are held upright and outward near the center of the rosette and become progressively more relaxed towards the outer whorls of foliage.

*Apex*.—Broad abruptly acute.

*Base*.—Long cuneate.

*Margin*.—Entire.

*Pubescence, texture and luster of the adaxial surface*.—Glabrous, smooth, and glaucescent.

*Pubescence, texture and luster of the abaxial surface*.—Glabrous, smooth, and glaucescent.

*Color*.—Juvenile foliage, adaxial surface — Brown, nearest to 200C, and suffused with greyed-purple distally, nearest to in between RHS 187B and 187C; fading to greyed-red towards the base, nearest to in between RHS 182C and 182D; margined greyed-red, nearest to RHS 182C. Leaves are covered with a thin layer of epicuticular wax which is colored greyed-purple, nearest to RHS N187C. Juvenile foliage, abaxial surface — Brown, nearest to 200C, and suffused with greyed-purple distally, nearest to RHS 187A; fading to greyed-red towards the base, nearest to in between RHS 182C and 182D; margined greyed-red, nearest to RHS 182C. Leaves are covered with a thin layer of epicuticular wax which is colored greyed-purple, nearest to RHS N187C. Mature foliage, adaxial surface — Greyed-orange, nearest to RHS 177A; suffused with brown distally, nearest to RHS 200C; margined greyed-green, nearest to RHS 195B; fading to greyed-red towards the base, nearest to RHS 182C. Leaves are covered with a thin layer of epicuticular wax which is colored greyed-green, nearest to in between RHS 198A and 198B. Mature foliage, abaxial surface — Nearest to in between yellow-green and greyed-green, RHS 148A and 197A, and margined greyed-green, nearest to RHS 195B; fading to greyed-brown towards the base, nearest to RHS 199B. Leaves are covered with a thin layer of epicuticular wax which is colored greyed-green, nearest to in between RHS 198A and 198B.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'Serena' differ from the parent, an unnamed *Echeveria* hybrid plant (not patented) in the following characteristics described in Table 1 below.

TABLE 1

| Characteristic | 'Serena' | The parent. |
|---|---|---|
| Foliage aspect. | Inverted carinate. | Flat. |
| Foliage aspect. | Varying from convex to concave, creating a wavy appearance, with the leaf tip curled upward. | Distal portion of the leaf margins and tip are curled upward. |
| General coloration of the foliage. | Greyed-purple with a weaker pink hue. | Greyed-purple with a stronger pink hue. |

COMPARISONS WITH THE CLOSEST KNOWN COMPARATOR

Plants of the new cultivar 'Serena' differ from the species *Echeveria* hybrid 'AMIECH1819' (U.S. Plant Pat. No. 31,493), which is the closest known comparator, in the following characteristics described in Table 2 below.

TABLE 2

| Characteristic | 'Serena' | 'AMIECH1819' |
|---|---|---|
| Foliage aspect. | Varying from convex to concave, creating a wavy appearance, with the leaf tip curled upward. | Moderately to strongly convex and moderately to strongly revolute to near-tubular; foliage is slightly curved upwards. |
| Presence of irregularly globular growths on the foliage. | Not present. | Present. |
| Color of the epicuticular wax. | Greyed-purple. | Black. |
| General coloration of the foliage. | Greyed-purple with a stronger pink hue. | Greyed-purple with a weaker pink hue. |

That which is claimed is:

1. A new and distinct variety of *Echeveria* plant named 'Serena', substantially as described and illustrated herein.

* * * * *